(12) United States Patent
Kim et al.

(10) Patent No.: US 12,115,159 B2
(45) Date of Patent: Oct. 15, 2024

(54) PHARMACEUTICAL COMPOSITION FOR PREVENTING OR TREATING NONALCOHOLIC FATTY LIVER DISEASE, CONTAINING GPR119 LIGAND AS ACTIVE INGREDIENT

(71) Applicant: DONG-A ST CO., LTD., Seoul (KR)

(72) Inventors: Mi-Kyung Kim, Suwon-Si (KR); Bo Ram Lee, Yongin-Si (KR); Hansu Park, Suwon-Si (KR); Seung Ho Lee, Yongin-Si (KR); Yu Na Chae, Yongin-Si (KR)

(73) Assignee: Dong-A St Co., Ltd. (KR)

( * ) Notice: Subject to any disclaimer, the term of this patent is extended or adjusted under 35 U.S.C. 154(b) by 458 days.

(21) Appl. No.: 17/275,555

(22) PCT Filed: Sep. 11, 2019

(86) PCT No.: PCT/KR2019/011839
§ 371 (c)(1),
(2) Date: Mar. 11, 2021

(87) PCT Pub. No.: WO2020/055170
PCT Pub. Date: Mar. 19, 2020

(65) Prior Publication Data
US 2022/0047591 A1    Feb. 17, 2022

(30) Foreign Application Priority Data

Sep. 12, 2018  (KR) .......................... 10-2018-0109219

(51) Int. Cl.
*A61K 31/506* (2006.01)
*A23L 33/10* (2016.01)
*A61P 1/06* (2006.01)

(52) U.S. Cl.
CPC ............ *A61K 31/506* (2013.01); *A23L 33/10* (2016.08); *A61P 1/06* (2018.01)

(58) Field of Classification Search
CPC .......... A61K 31/506; A23L 33/10; A61P 1/06
See application file for complete search history.

(56) References Cited

U.S. PATENT DOCUMENTS

| | | | |
|---|---|---|---|
| 9,895,370 | B2 | 2/2018 | Kang et al. |
| 10,428,055 | B2 | 10/2019 | Yang et al. |
| 2006/0154866 | A1 | 7/2006 | Chu et al. |
| 2011/0212939 | A1 | 9/2011 | Bertram et al. |
| 2012/0053180 | A1 | 3/2012 | Kang et al. |
| 2013/0310331 | A1 | 11/2013 | Joubert et al. |
| 2014/0051714 | A1 | 2/2014 | Jones |
| 2017/0049773 | A1 * | 2/2017 | Kang ............... A61K 31/427 |
| 2019/0008864 | A1 | 1/2019 | Kang et al. |
| 2019/0092763 | A1 | 3/2019 | Yang et al. |
| 2023/0117286 | A1 * | 4/2023 | Kim ............... A61K 31/192 514/171 |
| 2023/0143119 | A1 | 5/2023 | Kim et al. |

FOREIGN PATENT DOCUMENTS

| | | |
|---|---|---|
| CA | 2959714 | 5/2016 |
| CA | 3113579 | 3/2020 |
| CA | 3167630 | 9/2021 |
| CA | 3168474 | 9/2021 |
| CN | 101128192 | 2/2008 |
| CN | 107074838 | 8/2017 |
| CN | 106459170 | 8/2020 |
| EA | 025484 | 12/2016 |
| EP | 3212640 | 9/2017 |
| EP | 3827829 | 6/2021 |
| JP | 2008-526235 | 7/2008 |
| JP | 2013538862 | 10/2013 |
| JP | 2017-517483 | 6/2017 |
| JP | 2017533213 | 11/2017 |
| KR | 10-2007-0095400 | 9/2007 |
| KR | 10-2015-0018916 | 2/2015 |
| KR | 10-2015-0018916 A | 2/2015 |
| KR | 10-2015-0088204 A | 7/2015 |
| KR | 10-2016-0049434 A | 5/2016 |
| KR | 10-2016-0143724 | 12/2016 |
| RU | 2465896 | 11/2012 |
| RU | 2012145116 | 4/2014 |
| RU | 2670197 | 10/2018 |
| WO | WO 2006076231 | 7/2006 |
| WO | WO 2008130584 | 10/2008 |

(Continued)

OTHER PUBLICATIONS

Double Patenting over copending U.S. Appl. No. 17/905,912 (US20230117286A1). (Year: 2023).*
U. Bahirat et al. APD668, a G protein-coupled receptor 119 agonist improves fat tolerance and attenuates fatty liver in high-trans fat diet induced steatohepatitis model in C57BL/6 mice. Eur J Pharmacol. Apr. 15, 2017;801:35-45. doi: 10.1016/j.ejphar.2017.02.043. Epub Mar. 6, 2017. PMID: 28274625. (Year: 2017).*
M. Kato et al. Safety and Pharmacokinetics of DS-8500a, a Novel GPR119 Agonist, After Multiple Oral Doses in Healthy Japanese Males. Clin Drug Investig. Jun. 2018;38(6):519-525. doi: 10.1007/s40261-018-0633-5. PMID: 29582248. (Year: 2018).*

(Continued)

*Primary Examiner* — Robert H Havlin
*Assistant Examiner* — Manahil Mirghani Ali Abdalhameed
(74) *Attorney, Agent, or Firm* — Fish & Richardson P.C.

(57) ABSTRACT

The present invention pertains to a pharmaceutical composition for preventing or treating non-alcoholic fatty liver disease, the composition containing G protein coupled receptor 119 (GPR119) ligand as an active ingredient. The pharmaceutical composition according to the present invention exhibits the excellent effects of improving lipid metabolism, reducing fat accumulation in liver tissues, and preventing histological damage caused by inflammation and fibrosis in liver tissues, and can thus be useful in preventing or treating non-alcoholic fatty liver disease.

5 Claims, 8 Drawing Sheets

(56) References Cited

FOREIGN PATENT DOCUMENTS

| WO | WO 2010004347 | | 1/2010 | | |
|---|---|---|---|---|---|
| WO | WO 2010015664 | | 2/2010 | | |
| WO | WO 2011118976 | | 9/2011 | | |
| WO | WO 2012006955 | | 1/2012 | | |
| WO | WO 2012145604 | | 10/2012 | | |
| WO | 2015020333 | A1 | 2/2015 | | |
| WO | 2015111971 | A1 | 7/2015 | | |
| WO | WO 2015155140 | | 10/2015 | | |
| WO | WO-2016068453 | A1 * | 5/2016 | ............. | A61K 31/42 |
| WO | WO 2017106112 | | 6/2017 | | |
| WO | WO 2018153849 | | 8/2018 | | |

OTHER PUBLICATIONS

J. Yang et al. GPR119: a promising target for nonalcoholic fatty liver disease. FASEB J. Jan. 2016;30(1):324-35. doi: 10.1096/fj.15-273771. Epub Sep. 23, 2015. PMID: 26399788. (Year: 2016).*
Extended Search Report in European Appln. No. 19860397.9, dated May 6, 2022, 8 pages.
Kim et al., "A novel GPR119 agonist DA-1241 preserves pancreatic function via the suppression of ER stress and increased PDX1 expression," Biomedicine & Pharmacotherapy, 2021, 144:112324.
Jun, "Practice Guideline for the Diagnosis and Management of Non-alcoholic Fatty Liver Disease", Korean J. Gastroenterol. vol. 60, No. 1, pp. 64-66 (with English Abstract).
Office Action in Indian Appln. No. 202137016429, dated Jun. 8, 2021, 5 pages (with English Translation).
Office Action in Korean Appln. No. 10-2019-0112561, dated Nov. 12, 2021, 10 pages (with English translation).
Office Action and Search Report in Russian Appln. No. 2021109691, dated Sep. 17, 2021, 27 pages (with English Translation).
Office Action in Korean Appln. No. 10-2019-0112561, dated Nov. 12, 2020, 10 pages (with English Translation).
Bahirat et al., "APD668, a G protein-coupled receptor 119 agonist improves fat tolerance and attenuates fatty liver in high-trans fat diet induced steatohepatitis model in C57BL/6 mice," European Journal of Pharmacology, 2017, 801:35-45, doi: 10.1016/j.ejphar.2017.02.043.
Bahirat et al., "Combination of APD668, a G protein-coupled receptor 119 agonist with linagliptin, a DPPIV inhibitor, prevents progression of steatohepatitis in a murine model of non-alcoholic steatohepatitis with diabetes," Medical Molecular Morphology, 2019, 52(1):36-43, https://doi.org/10.1007/s00795-018-0200-4.
Office Action in Australian Appln. No. 2019337286, dated Feb. 3, 2022, 10 pages.
Office Action in Japanese Appln. No. 2021-513203, dated Apr. 13, 2022, 8 pages (with English Translation).
Yang et al., "Therapeutic application of GPR119 ligands in metabolic disorders," Accepted Article, Diabetes, Obesity and Metabolism, 2018, 20(2):257-269, doi: 10.1111/dom.13062.
International Search Report for PCT/KR2019/011839, mailed on Jan. 2, 2020. 3 pages.
Yang et al., "GPR119: a promising target for nonalcoholic fatty liver disease", The FASEB Journal 2016 vol. 30 pp. 324-335.
Hu et al., "A lincRNA-DYNLRB2-2/GPR119/GLP-1R/ABCA1-dependent signal transduction pathway is essential for the regulation of cholesterol homeostasis", Journal of Lipid Research, vol. 55, 2014, pp. 681-697.
Jun, "Practice Guideline for the Diagnosis and Management of Non-aocoholic Fatty Liver Disease", Korean J Gastroenterol vol. 60, No. 1, pp. 64-66.
Chalasani, et al., "The Diagnosis and Management of Non-Alcoholic Fatty Liver Disease: Practice Guideline by the American Association fo the Study of Liver Diseases, American College of Gastoenterology, and the American Gastroenterological Association", Hepatology, vol. 55, No. 6, Jun. 2012, pp. 2005-2023.
Office Action for KR10-2019-0112561 dated Jan. 12, 2021 and English translation, 10 pages.
Yang et al., "GPR119: A Promising Target for Nonalcoholic Fatty Liver Disease," The FASEB Journal, Jan. 2016, 30(1):324-35.
Office Action in Chinese Appln. No. 201980059145.X, dated Mar. 24, 2023, 19 pages (with English Translation).
[No Author], "A Study to Evaluate the Safety, Tolerability, PK and PD of DA-1241 in Healthy Male Subjects," ClinicalTrails.gov, Nov. 20, 2017, 11 pages, retrieved from https://clinicaltrials.gov/study/NCT03061981.
Dyson G. & May P.'s Chemistry of Synthetic Drugs, translated from English. Mir, 1964, pp. 12-19 (with English Translation).
Extended European Search Report in European Appln. No. 21768861.3, mailed on Jan. 29, 2024, 10 pages.
International Search Report in International Appln. No. PCT/KR2021/002990, dated Jun. 24, 2021, 12 pages (with English Translation).
Kharkevich, D.A., Pharmacology: Textbook, 2010, 10th ed., M.: Geotar-Media, pp. 72-82 (with English Translation).
Knunyants et al., Chemical Encyclopedic Dictionary, Moscow, Soviet Encyclopedia, 1983, pp. 130-131 & 533-534.
Office Action and Search Report in Russian Appln. No. 2022124765, dated Apr. 10, 2023, 25 pages (with English Translation).
Office Action in Australian Appln. No. 2021235294, mailed on Sep. 12, 2023, 4 pages.
Office Action in Chinese Appln. No. 202180019079.0, mailed on Jan. 20, 2024, 16 pages (with English Translation).
Office Action in Japanese Appln. No. 2022-554634, mailed on Sep. 6, 2023, 11 pages (with English translation).
Office Action in Saudi Arabian Appln. No. 522440429, dated Mar. 22, 2023, 11 pages (with English Translation).
Smirnova et al., "Optical isomerism and biological activity of pharmaceutical preparations," Bulletin of Moscow University, Series 2 Chemistry, 2012, 53(3):147-156 (with English Translation).
STN Database Search Report, dated Nov. 18, 2022, 16 pages.
V.G. Belikov's Pharmaceutical Chemistry, 4th ed., 2007, MEDpress-inform, Moscow, pp. 27-29 (with English Translation).
Vengerovsky, A.I., Pharmacological Incompatibility, Lecture for Doctors, Scientific and Educational Process: Methodical Seminar, Bulletin of Siberian Medicine, 2003, 3:49-56 (with English Translation).
Verma et al., "Predictive value of ALT levels for non-alcoholic steatohepatitis (NASH) and advanced fibrosis in non-alcoholic fatty liver disease (NAFLD)," Liver International, 2013, 1398-1405.

* cited by examiner

PHARMACEUTICAL COMPOSITION FOR PREVENTING OR TREATING NONALCOHOLIC FATTY LIVER DISEASE, CONTAINING GPR119 LIGAND AS ACTIVE INGREDIENT

CROSS-REFERENCE TO RELATED APPLICATIONS

This application is a U.S. National Phase application under 35 U.S.C. § 371 of International Patent Application No. PCT/KR2019/011839, filed Sep. 11, 2019, which claims priority to South Korean Application No. 10-2018-0109219, filed Sep. 12, 2018. The contents of the prior applications are hereby incorporated by reference in their entirety.

TECHNICAL FIELD

The present invention relates to a pharmaceutical composition, a food composition, and a feed composition for preventing or treating non-alcoholic fatty liver disease, comprising G protein coupled receptor 119 (GPR119) ligands as an effective ingredient; a method for treating and ameliorating non-alcoholic fatty liver disease; or a use thereof in preventing or treating non-alcoholic fatty liver disease.

BACKGROUND

Fatty liver is a pathological condition in which triglycerides are excessively accumulated in hepatocytes, and medically defined as a condition in which triglycerides account for 5% or more of a liver weight. Fatty liver is classified into alcoholic and non-alcoholic fatty livers depending on whether fatty liver is caused by excessive alcohol intake or not. Non-alcoholic fatty liver disease (NAFLD) is a group of diseases that encompass all aspects of the disease ranging from non-alcoholic fatty liver to steatohepatitis and cirrhosis. Simple non-alcoholic fatty liver, which has only fat deposits in the liver and shows an increase in fat deposits in liver tissues caused by insulin resistance, etc. without any findings of damage to hepatocytes and fibrosis, progresses into non-alcoholic steatohepatitis (NASH), which is accompanied by damage to hepatocytes caused by inflammatory responses due to oxidative stress and sometimes fibrosis, and may progress into liver cirrhosis, which is accompanied by irreversible liver damage if not treated properly.

Recently, a prevalence rate of non-alcoholic fatty liver disease has rapidly increased worldwide, and a prevalence rate of simple fatty liver is estimated to be 6.3 to 33%, and a prevalence rate of non-alcoholic steatohepatitis accompanied by inflammation is reported to be 3 to 5% (Hepatology, 2012(55): 2005-2023). Simple fatty liver very slowly progresses to serious liver disease and does not increase a mortality rate associated with liver disease, but steatohepatitis may lead to cirrhosis and liver cancer and increases a mortality rate associated with liver disease as well as an overall mortality. In addition, simple fatty liver may be easily ameliorated if a weight loss is made by 3 to 5% through revision of general living habits, but it is recommended to make a weight loss by at least 10% for reduction of inflammation. However, it is not clear whether or not this weight loss may induce inflammation and fibrosis to be ameliorated in the liver (Korean J Gastroenterol, 2012(60): 64-66).

So far, there has not been a therapeutic agent for non-alcoholic steatohepatitis. If the disease worsens, a liver transplantation is performed. According to U.S. statistical data, hepatitis C has been considered as the most common cause of liver transplantation, followed by non-alcoholic steatohepatitis as of 2013. In addition, an increase rate of liver transplantation for 10 years from 2004 was 14% for hepatitis C, while 170% for non-alcoholic steatohepatitis showing rapid increase and NASH is also expected to become the first cause of liver transplantation since 2020, leaving hepatitis C behind, and thus there is an urgent need to develop an effective therapeutic agent for non-alcoholic fatty liver disease including non-alcoholic steatohepatitis.

Currently, a drug therapy for non-alcoholic steatohepatitis includes a method of taking in an insulin resistance enhancer (e.g., pioglitazone) or an antioxidant (e.g., vitamin E), in which findings of fat accumulation and inflammation amelioration have been confirmed through small-scale clinical trials in patients with non-alcoholic steatohepatitis. However, such method has failed to show a clear effect of ameliorating inflammation and fibrosis, and it is still impossible to provide those drugs as an intensive therapeutic option due to safety concerns about a long-term use.

G protein-coupled receptor 119 (GPR119) is distributed in L and K cells of the small intestine. If GPR119 is activated by triglyceride metabolites (2-monoacylglycerol), etc., GPR119 increases secretion of incretin hormones such as glucagon-like peptide-1 (GLP-1) or glucose-dependent insulinotropic polypeptide (GIP). GPR119 is also distributed in pancreatic beta cells and alpha cells and contributes to maintaining blood sugar levels by controlling secretion of insulin and glucagon in a glucose-dependent manner. In addition, it is reported that, if GPR119 is overexpressed in a human macrophage line, an expression of GLP-1 receptor is increased to raise ATP-binding cassette protein A1 (ABCA1), which is a transporter of taking cholesterol out of cells, thereby increasing an ApoA1-mediated reflux of cholesterol, improving lipid metabolism, and decreasing a concentration of inflammatory cytokines in blood (J Lipid Res, 2014(55): 681-697).

However, it has not yet been reported if GPR119 ligand directly inhibits an inflammatory response and thus inhibits the inflammatory response, which is the core of hepatocyte damage in non-alcoholic fatty liver disease. Also, it has not been reported if GPR119 ligand ameliorates inflammation and fibrosis after the induction of non-alcoholic fatty liver disease.

DETAILED DESCRIPTION OF THE INVENTION

Technical Problem

An object of the present invention is to provide a pharmaceutical composition for preventing or treating non-alcoholic fatty liver disease comprising GPR119 ligand as an effective ingredient.

Technical Solution

The present invention may provide a pharmaceutical composition for preventing or treating non-alcoholic fatty liver disease, which comprises a compound represented by a following chemical formula 1, pharmaceutically acceptable salts thereof, optical isomers thereof, hydrates or solvates thereof, or mixtures thereof as an effective ingredient:

[Chemical Formula 1]

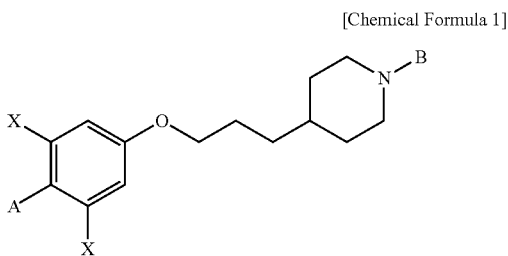

The pharmaceutical composition according to the present invention may be useful in preventing or treating non-alcoholic fatty liver disease by remarkably inhibiting triglyceride deposition, inflammation and fibrosis in liver tissues.

In the chemical formula 1,

A is oxadiazole, dihydrooxazole, thiazole, or thiadiazole, the A is independently unsubstituted or substituted with at least one substituent selected from the group consisting of halogen, C1-C6 straight or branched-chain alkyl and C1-C6 hydroxyalkyl, and the alkyl or hydroxyalkyl group is independently unsubstituted or substituted with halogen or C1-C6 alkoxy group;

B is pyridine, pyrimidine, pyrazine, or oxadiazole, the B is independently unsubstituted or substituted with at least one substituent selected from the group consisting of halogen, C1-C6 straight or branched-chain alkyl, C1-C6 hydroxyalkyl, C1-C6 alkoxy and oxadiazole group, and the C1-C6 straight or branched-chain alkyl, C1-C6 hydroxyalkyl, C1-C6 alkoxy or oxadiazole group is independently unsubstituted or substituted with halogen, C1-C6 alkyl or C1-C6 alkoxy group; and X is each independently F, Cl, Br or I, but not limited thereto.

According to one embodiment of the present invention, in the chemical formula 1, it may be provided that
the A is

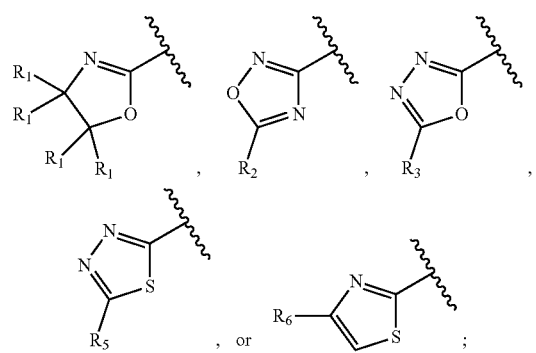

and

R1 to R3, R5 and R6 are each independently one or more substituents selected from the group consisting of hydrogen, halogen, C1-C6 straight or branched-chain alkyl and C1-C6 hydroxyalkyl, and the alkyl or hydroxyalkyl group is independently unsubstituted or substituted with halogen or C1-C6 alkoxy group.

According to another embodiment of the present invention, in the chemical formula 1,
it may be provided that
B is

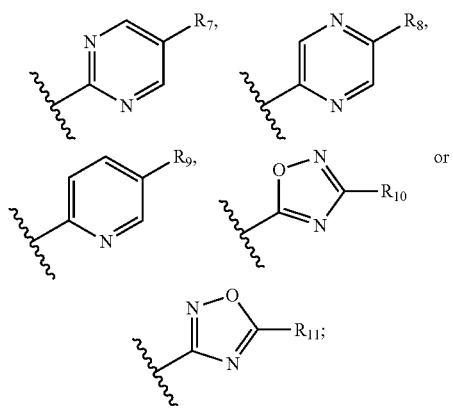

and
the R7 to R11 are independently substituted with at least one substituent selected from the group consisting of hydrogen, halogen, C1-C6 straight or branched-chain alkyl, C1-C6 hydroxyalkyl, C1-C6 alkoxy and oxadiazole group, and the alkyl, alcohol, alkoxy or oxadiazole group is independently unsubstituted or substituted with halogen, C1-C6 alkyl or C1-C6 alkoxy group.

According to one embodiment of the present invention, in the chemical formula 1, it may be provided that A is oxadiazole substituted with C1-C6 straight or branched-chain alkyl, B is pyrimidine substituted with C1-C6 straight or branched-chain alkyl, and X is F.

In the present invention, the term "halogen" may refer to fluorine, chlorine, bromine or iodine.

In the present invention, the term "alkyl" may refer to a straight-chain or branched-chain hydrocarbon residue unless otherwise noted. An example of the C1-C6 alkyl may include methyl, ethyl, propyl, isopropyl, butyl, isobutyl, pentyl, hexyl, etc.

In the present invention, the term "alkoxy" may include an alkyl-oxygen radical having alkyl as defined above unless otherwise noted. An example of the C1-C6 alkoxy may include methoxy, ethoxy, propoxy, butoxy, pentoxy, etc.

In the present invention, the term "heterocycle" or "heterocyclic" may refer to 5 to 13-membered hetero-aromatic or non-aromatic compound including one to three heteroatoms selected from the group consisting of N, O, and S unless otherwise noted.

In the present invention, the compound represented by the chemical formula 1 may be a compound specifically selected from the group consisting of the following compounds:

2-(4-(3-(1-(5-ethylpyrimidine-2-yl)piperidine-4-yl)propoxy)-2,6-difluorophenyl)-4,5-dihydrooxazole, (R)-2-(4-(3-(1-(5-ethylpyrimidine-2-yl)piperidine-4-yl)propoxy)-2,6-difluorophenyl)-4-methyl-4,5-dihydrooxazole, (S)-2-(4-(3-(1-(5-ethylpyrimidine-2-yl)piperidine-4-yl)propoxy)-2,6-difluorophenyl)-4-methyl-4,5-dihydrooxazole, (S)-2-(4-(3-(1-(5-ethylpyrimidine-2-yl)piperidine-4-yl)propoxy)-2,6-difluorophenyl)-5-methyl-4,5-dihydrooxazole, (R)-2-(4-(3-(1-(5-ethylpyrimidine-2-yl)piperidine-4-yl) propoxy)-2,6-difluorophenyl)-5-methyl-4,5-dihydrooxazole, 2-(4-(3-(1-(5-ethylpyrimidine-2-yl)piperidine-4-yl) propoxy)-2,6-difluorophenyl)-5,5-dimethyl-4,5-dihydrooxazole, (R)-(2-(4-(3-(1-(5-ethylpyrimidine-2-yl)piperidine-4-yl) propoxy)-2,6-difluorophenyl)-4,5-dihydrooxazole-5-yl) methanol, (S)-(2-(4-(3-(1-(5-ethylpyrimidine-2-yl)piperidine-4-yl) propoxy)-2,6-difluorophenyl)-4,5-dihydrooxazole-5-yl) methanol, (R)-3-(2-(4-(3-(3,5-difluoro-4-(5-methyl-4,5-dihydrooxazole-2-yl)phenoxy)prop yl)piperidine-1-yl)pyrimidine-5-yl)-5-isobutyl-1,2,4-oxadiazole, (R)-5-(4-(3-(3,5-difluoro-4-(4-methyl-4,5-dihydrooxazole-2-yl)phenoxy)propyl) piperidine-1-yl)-3-isopropyl-1,2,4-oxadiazole, (S)-5-(4-(3-(3,5-difluoro-4-(5-methyl-4,5-dihydrooxazole-2-yl)phenoxy)propyl) piperidine-1-yl)-3-isopropyl-1,2,4-oxadiazole, 5-(4-(3-(4-(5,5-dimethyl-4,5-dihydrooxazole-2-yl)-3,5-difluorophenoxy)propyl) piperidine-1-yl)-3-isopropyl-1,2,4-oxadiazole, 3-(4-(3-(1-(5-ethylpyrimidine-2-yl)piperidine-4-yl) propoxy)-2,6-difluorophenyl)-5-methyl-1,2,4-oxadiazole, 3-(4-(3-(1-(5-ethylpyrimidine-2-yl)piperidine-4-yl) propoxy)-2,6-difluorophenyl)-5-propyl-1,2,4-oxadiazole, 3-(4-(3-(1-(5-ethylpyrimidine-2-yl)piperidine-4-yl) propoxy)-2,6-difluorophenyl)-5-isopropyl-1,2,4-oxadiazole, 5-(tert-butyl)-3-(4-(3-(1-(5-ethylpyrimidine-2-yl)piperidine-4-yl)propoxy)-2,6-difluorophenyl)-1,2,4-oxadiazole, (3-(4-(3-(1-(5-ethylpyrimidine-2-yl)piperidine-4-yl) propoxy)-2,6-difluorophenyl)-1,2,4-oxadiazole-5-yl) methanol, 2-(3-(4-(3-(1-(5-ethylpyrimidine-2-yl)piperidine-4-yl) propoxy)-2,6-difluorophenyl)-1,2,4-oxadiazole-5-yl)ethane-1-ol, (S)-1-(3-(4-(3-(1-(5-ethylpyrimidine-2-yl)piperidine-4-yl) propoxy)-2,6-difluoro phenyl)-1,2,4-oxadiazole-5-yl)propane-1-ol, (R)-1-(3-(4-(3-(1-(5-ethylpyrimidine-2-yl)piperidine-4-yl) propoxy)-2,6-difluoro phenyl)-1,2,4-oxadiazole-5-yl)propane-2-ol, (S)-1-(3-(4-(3-(1-(5-ethylpyrimidine-2-yl)piperidine-4-yl) propoxy)-2,6-difluoro phenyl)-1,2,4-oxadiazole-5-yl)propane-2-ol, 2-(3-(4-(3-(1-(5-ethylpyrimidine-2-yl)piperidine-4-yl) propoxy)-2,6-difluorophenyl)-1,2,4-oxadiazole-5-yl)-2-methylpropane-1-ol, 3-(2,6-difluoro-4-(3-(1-(5-propylpyrimidine-2-yl)piperidine-4-yl)propoxy)phenyl)-5-isopropyl-1,2,4-oxadiazole, 3-(2,6-difluoro-4-(3-(1-(5-pentylpyrimidine-2-yl)piperidine-4-yl)propoxy)phenyl)-5-isopropyl-1,2,4-oxadiazole, 3-(2,6-difluoro-4-(3-(1-(5-(trifluoromethyl)pyrimidine-2-yl)piperidine-4-yl)propoxy)phenyl)-5-isopropyl-1,2,4-oxadiazole, 3-(2,6-difluoro-4-(3-(1-(5-methoxypyrimidine-2-yl)piperidine-4-yl)propoxy)phenyl)-5-isopropyl-1,2,4-oxadiazole, 3-(2,6-difluoro-4-(3-(1-(5-isopropoxypyrimidine-2-yl)piperidine-4-yl)propoxy)phenyl)-5-isopropyl-1,2,4-oxadiazole, 3-(4-(3-(1-(5-chloropyrimidine-2-yl)piperidine-4-yl) propoxy)-2,6-difluorophenyl)-5-isopropyl-1,2,4-oxadiazole, 3-(4-(3-(1-(5-bromopyrimidine-2-yl)piperidine-4-yl) propoxy)-2,6-difluorophenyl)-5-isopropyl-1,2,4-oxadiazole, 3-(2,6-difluoro-4-(3-(1-(5-(5-isobutyl-1,2,4-oxadiazole-3-yl)pyrimidine-2-yl)piperidine-4-yl)propoxy)phenyl)-5-methyl-1,2,4-oxadiazole, 3-(2,6-difluoro-4-(3-(1-(5-(5-isobutyl-1,2,4-oxadiazole-3-yl)pyrimidine-2-yl)piperidine-4-yl)propoxy)phenyl)-5-ethyl-1,2,4-oxadiazole, 3-(2,6-difluoro-4-(3-(1-(5-(5-isobutyl-1,2,4-oxadiazole-3-yl)pyrimidine-2-yl)piperidine-4-yl)propoxy)phenyl)-5-isopropyl-1,2,4-oxadiazole, 5-(sec-butyl)-3-(2,6-difluoro-4-(3-(1-(5-(5-isobutyl-1,2,4-oxadiazole-3-yl)pyrimidine-2-yl)piperidine-4-yl) propoxy)phenyl)-1,2,4-oxadiazole, 3-(2,6-difluoro-4-(3-(1-(5-(5-isobutyl-1,2,4-oxadiazole-3-yl)pyrimidine-2-yl)piperidine-4-yl)propoxy)phenyl)-5-(methoxymethyl)-1,2,4-oxadiazole, (S)-1-(3-(2,6-difluoro-4-(3-(1-(5-(5-isobutyl-1,2,4-oxadiazole-3-yl)pyrimidine-2-yl)piperidine-4-yl)propoxy)phenyl)-1,2,4-oxadiazole-5-yl)propane-1-ol, 2-(3-(2,6-difluoro-4-(3-(1-(5-(5-isobutyl-1,2,4-oxadiazole-3-yl)pyrimidine-2-yl) piperidine-4-yl)propoxy)phenyl)-1,2,4-oxadiazole-5-yl)-2-methylpropane-1-ol, 3-(4-(3-(1-(5-chloropyrazine-2-yl)piperidine-4-yl) propoxy)-2,6-difluorophenyl)-5-isopropyl-1,2,4-oxadiazole, 3-(2,6-difluoro-4-(3-(1-(5-(trifluoromethyl)pyridine-2-yl) piperidine-4-yl)propoxy)phenyl)-5-isopropyl-1,2,4-oxadiazole, 3-(2,6-difluoro-4-(3-(1-(3-isopropyl-1,2,4-oxadiazole-5-yl) piperidine-4-yl)propoxy)phenyl)-5-methyl-1,2,4-oxadiazole, 3-(2,6-difluoro-4-(3-(1-(3-isopropyl-1,2,4-oxadiazole-5-yl) piperidine-4-yl)propoxy)phenyl)-5-isopropyl-1,2,4-oxadiazole, (3-(2,6-difluoro-4-(3-(1-(3-isopropyl-1,2,4-oxadiazole-5-yl)piperidine-4-yl)prop oxy)phenyl)-1,2,4-oxadiazole-5-yl)methanol, 2-(4-(3-(1-(5-ethylpyrimidine-2-yl)piperidine-4-yl) propoxy)-2,6-difluorophenyl)-5-methyl-1,3,4-oxadiazole, 2-ethyl-5-(4-(3-(1-(5-ethylpyrimidine-2-yl)piperidine-4-yl) propoxy)-2,6-difluorophenyl)-1,3,4-oxadiazole, 2-(4-(3-(1-(5-ethylpyrimidine-2-yl)piperidine-4-yl) propoxy)-2,6-difluorophenyl)-5-isopropyl-1,3,4-oxadiazole, 5-(4-(3-(1-(5-ethylpyrimidine-2-yl)piperidine-4-yl) propoxy)-2,6-difluorophenyl)-N-isopropyl-1,3,4-oxadiazole-2-amine, 2-(2,6-difluoro-4-(3-(1-(5-(trifluoromethyl)pyrimidine-2-yl)piperidine-4-yl)propoxy)phenyl)-5-methyl-1,3,4-oxadiazole, 2-(2,6-difluoro-4-(3-(1-(5-(trifluoromethyl)pyrimidine-2-yl)piperidine-4-yl)propoxy)phenyl)-5-ethyl-1,3,4-oxadiazole, 2-(2,6-difluoro-4-(3-(1-(5-(trifluoromethyl)pyrimidine-2-yl)piperidine-4-yl)propoxy)phenyl)-5-isopropyl-1,3,4-oxadiazole, 2-(4-(3-(1-(5-chloropyrazine-2-yl)piperidine-4-yl) propoxy)-2,6-difluorophenyl)-5-methyl-1,3,4-oxadiazole, 2-(4-(3-(1-(5-chloropyrazine-2-yl)piperidine-4-yl) propoxy)-2,6-difluorophenyl)-5-ethyl-1,3,4-oxadiazole, 2-(4-(3-(1-(5-chloropyrazine-2-yl)piperidine-4-yl) propoxy)-2,6-difluorophenyl)-5-isopropyl-1,3,4-oxadiazole, 5-(4-(3-(3,5-difluoro-4-(5-methyl-1,3,4-oxadiazole-2-yl) phenoxy)propyl)piperidine-1-yl)-3-propyl-1,2,4-oxadiazole, 5-(4-(3-(3,5-difluoro-4-(5-ethyl-1,3,4-oxadiazole-2-yl)phenoxy)propyl)piperidine-1-yl)-3-propyl-1,2,4-oxadiazole, 5-(4-(3-(3,5-difluoro-4-(5-isopropyl-1,3,4-oxadiazole-2-yl) phenoxy)propyl)piperidine-1-yl)-3-propyl-1,2,4-oxadiazole, 5-(4-(3-(3,5-difluoro-4-(5-methyl-1,3,4-oxadiazole-2-yl) phenoxy)propyl)piperidine-1-yl)-3-isopropyl-1,2,4-oxadiazole, 5-(4-(3-(4-(5-ethyl-1,3,4-oxadiazole-2-yl)-3,5-difluorophenoxy)propyl)piperidine-1-yl)-3-isopropyl-1,2,4-oxadiazole, 5-(4-(3-(3,5-difluoro-4-(5-isopropyl-1,3,4-oxadiazole-2-yl) phenoxy)propyl)piperidine-1-yl)-3-isopropyl-1,2,4-oxadiazole, 5-(4-(3-(3,5-difluoro-4-(5-methyl-1,3,4-oxadiazole-2-yl) phenoxy)propyl)piperidine-1-yl)-3-(2,2,2-trifluoroethyl)-1,2,4-oxadiazole, 3-(4-(3-(3,5-difluoro-4-(5-isopropyl-1,3,4-oxadiazole-2-yl) phenoxy)propyl)piperidine-1-yl)-5-isopropyl-1,2,4-oxadiazole, 2-(4-(3-(1-(5-ethylpyrimidine-2-yl)piperidine-4-yl) propoxy)-2,6-difluorophenyl)-5-isopropyl-1,3,4-thiadiazole, 2-(2,6-difluoro-4-(3-(1-(5-propylpyrimidine-2-yl)piperidine-4-yl)propoxy)phenyl)-5-isopropyl-1,3,4-thiadiazole, 2-(2,6-difluoro-4-(3-(1-(5-pentylpyrimidine-2-yl)piperidine-4-yl)propoxy)phenyl)-5-isopropyl-1,3,4-thiadiazole, 2-(2,6-difluoro-4-(3-(1-(5-fluoropyrimidine-2-yl)piperidine-4-yl)propoxy)phenyl)-5-isopropyl-1,3,4-thiadiazole, 2-(2,6-difluoro-4-(3-(1-(5-(trifluoromethyl)pyrimidine-2-yl)piperidine-4-yl)propoxy)phenyl)-5-isopropyl-1,3,4-thiadiazole, 2-(2,6-difluoro-4-(3-(1-(5-(trifluoromethyl)pyridine-2-yl) piperidine-4-yl)propoxy)phenyl)-5-isopropyl-1,3,4-thiadiazole, and 4-ethyl-2-(4-(3-(1-(5-ethylpyrimidine-2-yl)piperidine-4-yl) propoxy)-2,6-difluorophenyl)thiazole.

In an embodiment of the present invention, the compound represented by the chemical formula 1 of the present invention may be specifically 3-(4-(3-(1-(5-ethylpyrimidine-2-yl) piperidine-4-yl)propoxy)-2,6-difluorophenyl)-5-isopropyl-1,2,4-oxadiazole.

In the present invention, a non-limiting example of the pharmaceutically acceptable salt of the compound represented by the chemical formula 1 may include inorganic acid salts such as hydrochloric acid, bromic acid, phosphoric acid or sulfuric acid; organic carboxylic acid salts such as acetic acid, trifluoroacetic acid, citric acid, maleic acid, oxalic acid, succinic acid, benzoic acid, tartaric acid, fumaric acid, mandelic acid, ascorbic acid or malic acid, or sulfonic acid salts such as methanesulfonic acid or para-toluenesulfonic acid; alkali metal salts such as sodium, potassium or lithium; various acid salts known to be capable of forming other pharmaceutically acceptable salts; or the like.

In one specific embodiment of the present invention, it was confirmed through an experiment of conducting a histological examination, measuring the concentration of ALT and AST in blood, measuring the expression level of genes and proteins associated with inflammation and fibrosis and the like that damage to liver tissues, deposition of triglycerides in liver tissues, infiltration of inflammatory cells and fibrosis are remarkably inhibited in an ob/ob mouse model, in which non-alcoholic fatty liver disease has been induced by special diet, by administering the compound represented by the chemical formula 1 during the process of inducing the disease (Example 1).

In one specific embodiment of the present invention, it was confirmed for the first time that the compound represented by the chemical formula 1 inhibits a differentiation of human monocytes and an activation of differentiated macrophages by an inflammatory factor in a concentration-dependent manner through a mechanism for inhibiting inflammatory responses (Example 2).

In one specific embodiment of the present invention, it was confirmed that damage to liver tissues, deposition of triglycerides in liver tissues, infiltration of inflammatory cells and fibrosis are remarkably ameliorated in a C57BL6 mouse model, in which non-alcoholic fatty liver disease has been induced by special diet, by administering the compound represented by the chemical formula 1 after inducing the disease (Example 3).

The pharmaceutical composition for preventing or treating non-alcoholic fatty liver disease according to the present invention may be used in the form of a general pharmaceutical preparation. The pharmaceutical preparation may be administered in various oral and parenteral dosage forms upon administration, and the dosage form may be variously determined according to the method of use.

If the pharmaceutical preparation is formulated into various oral and parenteral dosage forms, it may be possible to use the generally used excipients such as fillers, diluents, extenders, binders, humectants, disintegrants, surfactants, etc.

A solid preparation for oral administration may include tablets, pills, powders, granules, capsules, etc., and this solid preparation may be prepared by mixing at least one excipient, for example, starch, calcium carbonate, sucrose, lactose, gelatin or the like in the pharmaceutical composition. In addition, lubricants such as magnesium stearate, talc, etc., may be used in addition to simple excipients.

Furthermore, a liquid preparation for oral administration may include suspending agents, liquids for internal use, emulsions, syrups, etc., but may also include various excipients, for example, humectants, sweetening agents, flavoring agents, preservatives, etc. in addition to water and liquid paraffin, which are the frequently used simple diluents.

A preparation for parenteral administration may include sterile aqueous solutions, non-aqueous solvents, suspensions, emulsions, lyophilized preparations and suppositories. The non-aqueous solvent and the suspending agent may include propylene glycol, polyethylene glycol, vegetable oil like olive oil, injectable ester like ethyl oleate, etc. A base of the suppository may include witepsol, macrogol, tween 61, cacao butter, laurinum, glycerogelatin, etc.

In addition, the pharmaceutical composition for preventing or treating non-alcoholic fatty liver disease according to the present invention may represent an effective amount in an administration range of about 1 to about 1,000 mg. An administered amount or an intake amount may be administered in a variety of administered doses and methods, such as once a day or several times a day by dividing the composition depending on the subject's body weight, age, gender, health condition, diet, administration time, administration method, excretion rate, and severity of the disease.

In the present invention, non-alcoholic fatty liver disease (NAFLD) may include both primary and secondary non-alcoholic fatty liver diseases. Specifically, in the present invention, non-alcoholic fatty liver disease (NAFLD) may include simple steatosis, non-alcoholic steatohepatitis (NASH) and liver fibrosis and liver cirrhosis caused by the progression of these diseases, but is not limited to.

The pharmaceutical composition of the present invention may comprise the compound represented by the chemical formula 1 or one or more effective ingredients which show a similar function thereto.

The present invention may also provide a method for preventing or treating non-alcoholic fatty liver disease, which includes administering a therapeutically effective amount of the compound represented by the chemical formula 1, pharmaceutically acceptable salts thereof, optical isomers thereof, hydrates or solvates thereof, or mixtures thereof into a subject in need of treatment.

In the present invention, the term "subject in need of treatment" may refer to mammals including humans, and the term "administration" may refer to providing a predetermined material to subjects by any appropriate method. The term "therapeutically effective amount" may refer to an amount of an active ingredient or a pharmaceutical composition which induces animals or humans to show the biological or medical responses considered by investigators, veterinarians, doctors or other clinicians, and such amount may include an amount thereof for inducing a relief of diseases or disorders to be treated. It is apparent to those skilled in the art that the therapeutically effective dosage and the number of administration for effective ingredients of the present invention may vary depending on a desired effect.

In the present invention, a route of administration of the pharmaceutical composition of the present invention may be administered through any general route as long as it can reach a target tissue.

Administration may be performed orally, intraperitoneally, intravenously, intramuscularly, subcutaneously, endothelially, intranasally, intrapulmonarily, rectally, intracavitarily, intraperitoneally and intrathecally, but is not limited thereto.

The pharmaceutical composition of the present invention may be administered once a day or at least twice a day at a certain interval of time.

The pharmaceutical composition of the present invention may be used alone or in combination with a surgery, endocrinotherapy, drug treatment and methods of using a biologic response modifier, in order to prevent and treat non-alcoholic fatty liver disease.

The present invention may also provide a food composition for preventing or ameliorating non-alcoholic fatty liver disease, which comprises the compound represented by the chemical formula 1, pharmaceutically acceptable salts thereof, optical isomers thereof, hydrates or solvates thereof, or mixtures thereof as an effective ingredient.

In the present invention, the term "alleviation" may refer to all the acts, in which a disease gets better or takes a favorable turn by administering the composition.

In the present invention, the term "food" may refer to meats, sausages, breads, chocolates, candies, snacks, confectioneries, pizzas, instant noodles, other noodles, chewing gums, dairy products including ice creams, various types of soup, beverages, teas, health drinks, alcohol beverages, vitamin complexes, health functional foods, health foods, health supplement foods and the like, and include all the foods in a conventional sense.

The term "health functional food" may be the same term as food for special health use (FoSHU), and refer to the food having a high medical and medicinal effect, which is processed to efficiently show a biological regulation function in addition to supplying nutrients. In this case, the term "function(ality)" may refer to controlling nutrients or obtaining a beneficial effect on health such as a physiological action, etc., with regard to the structure and function of the human body.

The "health food" may refer to food having an effect of actively maintaining or enhancing health compared to general food, and "health supplement food" may refer to food for a health supplement purpose. In some cases, the terms of health functional food, health food, and health supplement food may be used interchangeably.

The food of the present invention may be prepared by a method conventionally used in the art, and raw materials and ingredients conventionally added in the art may be added to prepare the food during the preparation. Specifically, proteins, carbohydrates, fats, nutrients, seasoning agents, and flavoring agents may be included, and an example of the carbohydrates may include glucose, fructose, maltose, sucrose, oligosaccharide, dextrin, cyclodextrin, xylitol, sorbitol, erythrol, saccharin or synthetic flavoring agents, but is not limited thereto. The food composition of the present invention may be prepared into various dosage forms without limitation, as long as the dosage form is recognized as food.

The present invention may also provide a method for preventing or ameliorating non-alcoholic fatty liver disease, which includes administering the food composition comprising the compound represented by the chemical formula 1, pharmaceutically acceptable salts thereof, optical isomers thereof, hydrate or solvates thereof, or mixtures thereof as an effective ingredient into a subject in need of amelioration.

The present invention may also provide a feed composition for preventing or ameliorating non-alcoholic fatty liver disease, which comprises the compound represented by the chemical formula 1, pharmaceutically acceptable salts thereof, optical isomers thereof, hydrates or solvates thereof, or mixtures thereof as an effective ingredient.

In the present invention, the term "feed" may refer to any natural or artificial diet, one meal, etc., or an ingredient of the one meal, which is to be consumed or digested by livestock or appropriate thereto. The feed may comprise feed additives or auxiliary feeds.

The kind of the feed is not particularly limited, and the feed conventionally used in the art may be used. A non-limiting example of the feed may include vegetable feeds such as grains, root fruits, food processing by-products, algae, fibers, pharmaceutical by-products, oils and fats, starches, oil meals, grain by-products or the like; animal feeds such as proteins, inorganic matters, oils and fats, minerals, single-cell proteins, zooplanktons, foods or the like. The feed may be used alone or by mixing at least two thereof.

The present invention may also provide a use of the compound represented by the chemical formula 1, pharmaceutically acceptable salts thereof, optical isomers thereof, hydrates or solvates thereof, or mixtures thereof in preventing or treating non-alcoholic fatty liver disease.

The present invention may also provide a use of the compound represented by the chemical formula 1, pharmaceutically acceptable salts thereof, optical isomers thereof, hydrates or solvates thereof, or mixtures thereof in preparing a pharmaceutical preparation for preventing or treating non-alcoholic fatty liver disease.

In the therapeutic method, the food composition, the alleviation method, the feed composition and the use thereof, the compound represented by the chemical formula 1 may be specifically 3-(4-(3-(1-(5-ethylpyrimidine-2-yl) piperidine-4-yl)propoxy)-2,6-difluorophenyl)-5-isopropyl-1,2,4-oxadiazole.

Matters mentioned in the pharmaceutical composition, the therapeutic method, the food composition, the alleviation method, the feed composition and the use thereof according to the present invention are applied the same, if not contradictory to each other.

Advantageous Effects

A pharmaceutical composition according to the present invention shows an excellent effect of alleviating lipid metabolism, reducing fat accumulation in liver tissues, and preventing histological damage caused by inflammation and fibrosis of liver tissues, and thus can be useful in preventing or treating non-alcoholic fatty liver disease.

MODE FOR INVENTION

The features and advantages of the present invention as well as methods for achieving them will be apparent with reference to exemplary embodiments described in detail hereinafter. However, the present invention is not limited to the Examples disclosed hereinafter, but will be implemented in various different forms. Hereinafter, the following Examples will be suggested for better understanding of the present invention and are provided only for the purpose of completely illustrating the scope of the present invention to those skilled in the art, and thus the present invention will be defined only by the scope of the claims thereto.

<Example 1> Confirmation of Efficacy of GPR119 Ligand in Mouse Model with Induced Steatohepatitis Due to Supply of Special Diet In order to confirm an effect of a GPR119 ligand compound according to the present invention on preventing non-alcoholic fatty liver disease, a following experiment was performed.

Preparation of Mouse Model with Non-Alcoholic Steatohepatitis

A six-week-old male ob/ob mouse with leptin deficiency was fed with a special diet containing high fat, high fructose, and high cholesterol for 10 weeks, and thus was induced to develop non-alcoholic steatohepatitis. A mixed form of diet was prepared so that a daily dose of (3-(4-(3-(1-(5-ethylpyrimidin-2-yl)piperidin-4-yl)propoxy)-2,6-difluorophenyl)-5-isopropyl-1,2,4-oxadiazole (hereinafter, "compound 1") reaches 100 mg/kg/day in the compound represented by the chemical formula 1, and supplied to the mouse from a time point of starting the supply of the special diet for 10 weeks.

Histological Examination

For a histological examination, the prepared mouse model with induced non-alcoholic steatohepatitis was subjected to autopsy to fix an isolated liver tissue in 10% formalin and prepare a paraffin block, thereby obtaining a 2 μm-thick tissue section. To confirm infiltration of inflammatory cells, Hematoxylin and Eosin (HE) stain was performed using an automatic staining machine (Autostainner XL, Leica), and the results thereof are shown in FIGS. 1 and 2.

Figure 1:
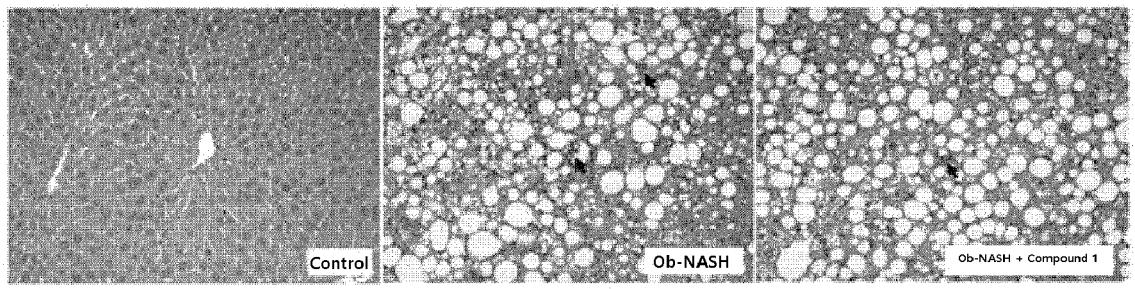
FIG. 1 is a picture of a tissue sample showing an effect of reducing triglycerides and inhibiting infiltration of inflammatory cells by the compound of the present invention in a mouse model with induced non-alcoholic steatohepatitis.
Figure 2:
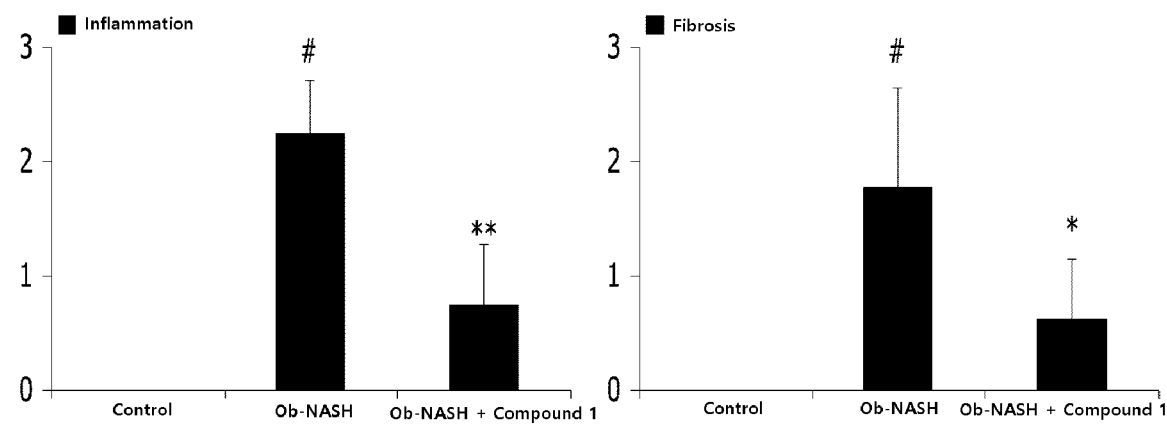
FIG. 2 is an analysis graph showing an effect of inhibiting infiltration of inflammatory cells and inhibiting fibrosis by the compound of the present invention in a mouse model with induced non-alcoholic steatohepatitis (#, $p<0.05$ vs. Normal; * & **, $p<0.05$ & $p<0.01$ vs. Ob-NASH).

As understood from FIGS. 1 and 2, the ob/ob mouse (Ob-NASH) fed with the special diet for 10 weeks showed a remarkable increase in triglycerides lipid droplets in liver tissues compared to C57BL/6 mouse fed with a normal diet (Normal), and the infiltration of inflammatory cells was also confirmed. In contrast, it was confirmed that the infiltration of inflammatory cells is significantly inhibited when the compound 1 of the present invention is simultaneously supplied with the special diet (Ob-NASH+Compd 1).

Figure 3:
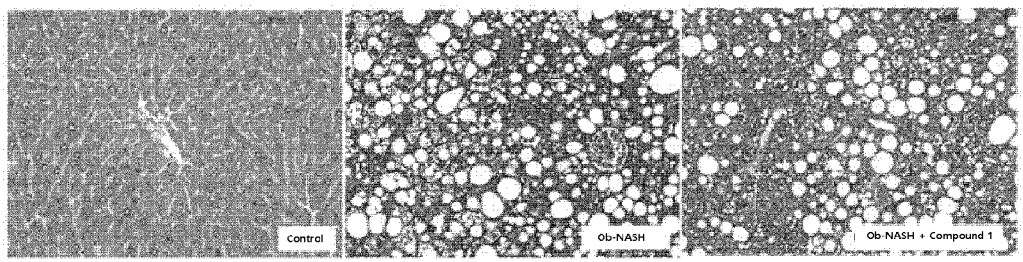
FIG. 3 is a picture of a tissue sample showing an effect of inhibiting fibrosis by the compound of the present invention in a mouse model with induced non-alcoholic steatohepatitis.

Then, for evaluation of fibrosis, fibers in liver tissue were specifically stained by using Masson's Trichrome stain or Sirius Res stain, and the results thereof are shown in FIGS. 2 and 3.

As understood from FIGS. 2 and 3, it was confirmed that the ob/ob mouse fed with the special diet for 10 weeks shows purple-colored liver tissues as a whole with a remarkable progress of fibrosis unlike the C57BL/6 mouse fed with the normal diet, but fibrosis of liver tissues is significantly inhibited when the compound 1 of the present invention is simultaneously supplied with the special diet.

AST and ALT Measurement in Blood

Figure 4:
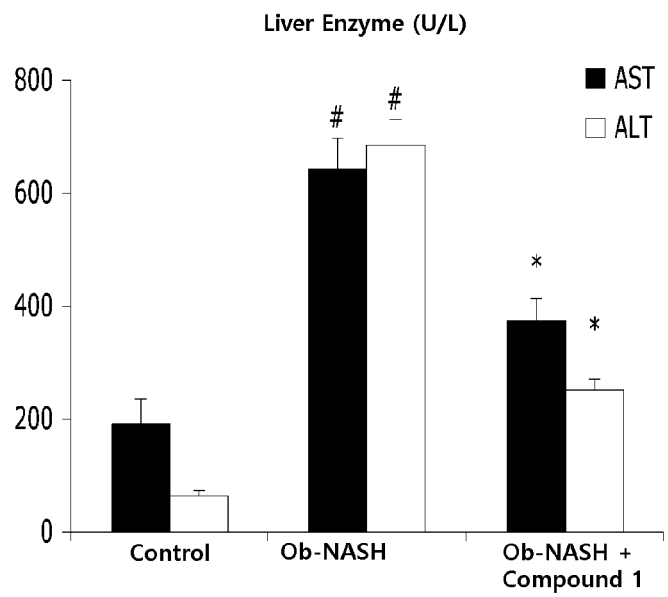
FIG. 4 is a view showing an effect of reducing AST and ALT by the compound of the present invention in a mouse model with induced non-alcoholic steatohepatitis (#, $p<0.05$ vs. Normal; *, $p<0.05$ vs. Ob-NASH).

The mouse model with induced non-alcoholic steatohepatitis was subjected to autopsy, after which plasma was separated therefrom, so as to quantify aspartate aminotransferase (AST) and alanine aminotransferase (ALT) by using an automatic blood analyzer (Konelab 20i), and the results thereof are shown in FIG. 4.

As shown in FIG. 4, it was confirmed that the ob/ob mouse fed with the special diet for 10 weeks shows a significant increase in ALT and AST levels in blood, which is a marker of liver damage, due to damage to liver tissues unlike the C57BL/6 mouse fed with the normal diet. On the other hand, it was confirmed that ob/ob mouse is administered compound 1 of the present invention together with the special diet shows a significant inhibition of increase in ALT and AST, which means that hepatocytes damage is alleviated.

Confirmation of Concentration of Proteins Associated with Inflammation and Fibrosis To evaluate an effect on the expression of inflammation-related genes and fibrosis-related proteins in liver tissues, the liver tissues obtained from the mouse model were put into RIPA buffer (Cell Signaling) and pulverized with TissueLyser II™ (Quiagen), after which a total protein concentration was quantified with Pierce BCA Protein Assay Kit (Thermo Fisher Scientific) and a protein concentration of Mouse Ccl2 (=Mcp1; R&D Systems, MJE00) and Timp1 (R&D Systems, MTM100) in the liver tissues was quantified by using a commercially available ELISA kit, so that the results thereof are shown in FIG. 5.

Figure 5:
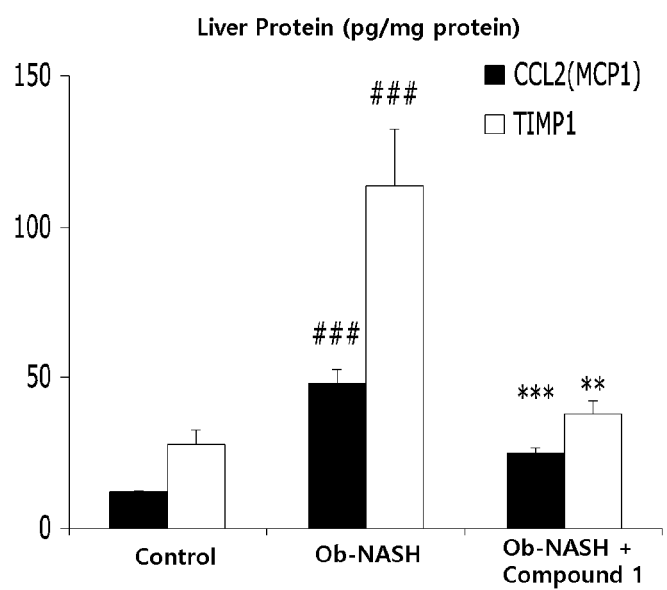
FIG. 5 is a view showing results of measuring a concentration of proteins associated with inflammation and fibrosis in a mouse model with induced non-alcoholic steatohepatitis (###, $p<0.001$ vs. Normal;  & *, $p<0.01$ & $p<0.001$ vs. Ob-NASH).

As shown in FIG. 5, it was confirmed that the mouse fed with the special diet shows an increase in protein concentrations of Ccl2 (=Mcp1), in the liver tissues with regard to Ccl2 (=Mcp1), which is a factor for inducing inflammatory cells to the liver tissues, and Timp1, an endogenous inhibitor for enzymes degrading fibers deposited in the liver tissues, while protein levels of Ccl2 and Timp1 are significantly inhibited when the compound 1 of the present invention is administered together with the special diet.

Confirmation of Expression of Genes Associated with Inflammation and Fibrosis

To measure an expression level of inflammation-related genes and fibrosis-related genes in liver tissues, Trizol® (Invitrogen) was added to the liver tissues collected from the mouse model, after which a total RNA was extracted from the tissues according to the method provided by the manufacturer, and then cDNA was synthesized by using a reverse transcriptase. Then, a real-time polymerase chain reaction was performed in LightCycler®480 Instrument II (Roche-LifeScience) equipment by using a reagent of SYBR Green I Master Mix (Roche, 04707516001), and the results thereof are shown in FIG. 6.

Figure 6:
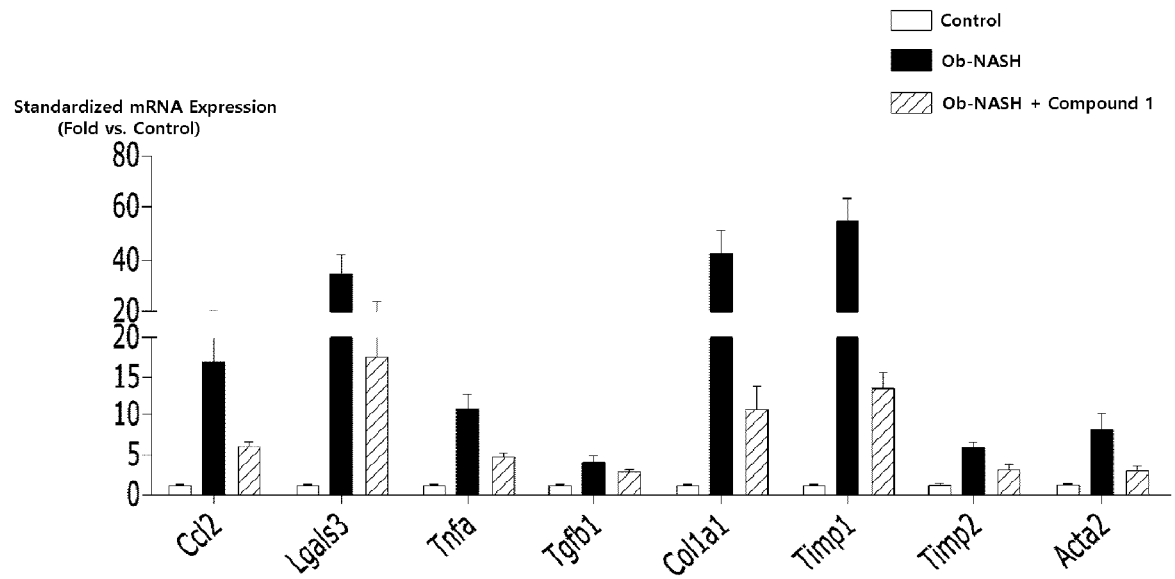
FIG. 6 is a view showing results of measuring an expression level of genes associated with inflammation and fibrosis in a mouse model with induced non-alcoholic steatohepatitis.

As shown in FIG. 6, it was confirmed that the mouse fed with the special diet for weeks shows an increase in expression of inflammation-related mouse genes (Ccl2, Lgals3, Tnfa) and fibrosis-related genes (Tgfb1, Col1a, Timp1, Timp2, Acta2), while the increase in expression of genes associated with inflammation and fibrosis is significantly inhibited when the compound 1 of the present invention is administered together with the special diet.

The above results suggest that the compound of the present invention has an excellent effect on non-alcoholic fatty liver disease by inhibiting damage, inflammation and fibrosis of liver tissues.

<Example 2> Confirmation of Inhibitory Effect on Differentiation of Human Monocytes and Activation of Differentiated Macrophages To evaluate a direct anti-inflammatory effect of the compound according to the present invention, the effect on the differentiation of human monocytes and the activation thereof was confirmed.

Figure 7:
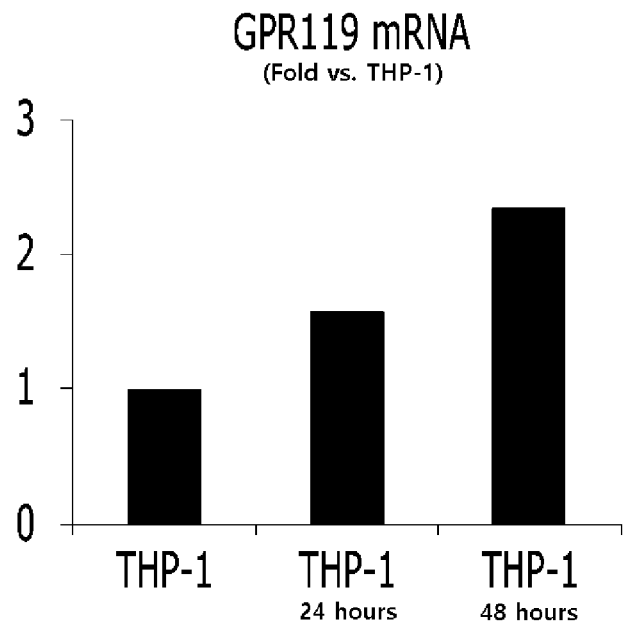
FIG. 7 is a view showing results of evaluating a gene expression of GPR119 in cells at a time point before differentiating human monocytes into macrophages and after differentiation for 24 and 48 hours.

First, as a result of evaluating a gene expression of GPR119 in cells at a time point before differentiating human monocytes (THP-1, ATCC® TIB-202™) into macrophages and after differentiation for 24 and 48 hours by using Phorbol 12-myristate 13-acetate (PMA), it was confirmed that an expression of GPR119 receptor increases with time as monocytes are differentiated into macrophages (FIG. 7).

Figure 8:
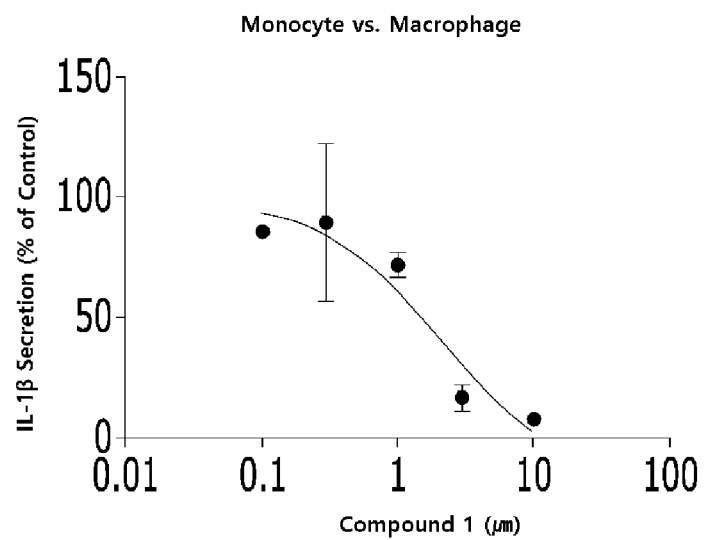
FIG. 8 is a view showing results of evaluating an effect on differentiation of human monocytes into macrophages according to treatment with the compound of the present invention.

Then, THP-1 monocytes were treated with PMA (50 ng/ml) for 48 hours to be differentiate into macrophages, while the compound 1 was co-treated, then replaced with serum-free medium, and then treated with lipopolysaccharides (LPS, 0.5 ng/ml) for four hours so as to quantity interleukin-1β (IL-1β, R&D Systems, DY201) secreted into the medium by using a commercialized ELISKA kit and evaluate an effect on the differentiation of monocytes, so that the results thereof are shown in FIG. 8.

As shown in FIG. 8, it was confirmed that IL-1β secretion caused by activation of macrophages is decreased in a concentration-dependent manner when treated with the compound of the present invention in a process of differentiating monocytes into macrophages.

In addition, after treating the differentiated macrophages with the compound 1 for 48 hours, the secreted IL-1β was quantified by the same method as above with regard to the activation of immune cells by LPS, so as to evaluate an effect on the activation of differentiated macrophages. Thus, the results thereof are shown in FIG. 9.

Figure 9:
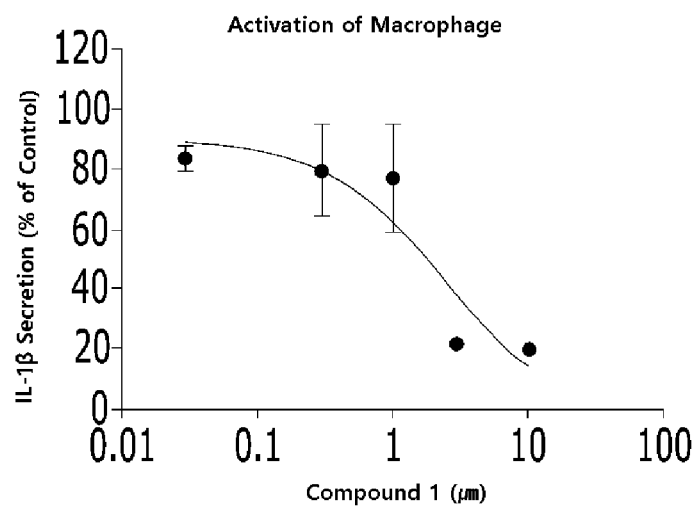
FIG. 9 is a view showing results of evaluating an effect on activation of differentiated macrophages according to treatment with the compound of the present invention.

As shown in FIG. 9, it was confirmed that IL-1β secretion caused by activation of macrophages is decreased in a concentration-dependent manner even when the differentiated macrophages are treated with the compound of the present invention.

The above results suggest that the compound of the present invention has an excellent effect on preventing and treating non-alcoholic fatty liver disease by directly inhibiting the differentiation and activation of immune cells.

<Example 3> Confirmation of Efficacy of GPR119 Ligand in Mouse Model with Induced Steatohepatitis Due to Supply of Special Diet In order to confirm an effect of a GPR119 ligand compound according to the present invention on treating non-alcoholic fatty liver disease, a following experiment was performed.

Preparation of a Mouse Model with Non-Alcoholic Steatohepatitis and Study Design A six-week-old male C57BL/6J mouse was fed with a special diet comprising high fat, high fructose, and high cholesterol for at least 26 weeks, and thus was induced to develop non-alcoholic steatohepatitis. It was confirmed that fatty liver and inflammatory fibrosis are induced through a biopsy of liver tissues three weeks before drug supply, and mice were evenly distributed into each group based on the area of collagen stained in the liver tissues. A feed was prepared by mixing the compounds according to the present invention in a special diet and supplied for additional eight weeks. According to the diet supplied to the mice, each of the groups was classified as a control group fed with a normal diet (Normal), a positive control group in which mice with induced non-alcoholic steatohepatitis due to the special diet were not supplied with a drug (DIO-NASH), and a group in which mice with induced non-alcoholic steatohepatitis were supplied with the compound 1 in an amount of 30 mg/kg/day (L) and 100 mg/mg/day (H) (Cmpd1 (L) and Cmpd1 (H), respectively).

Histological Examination

Figure 10:
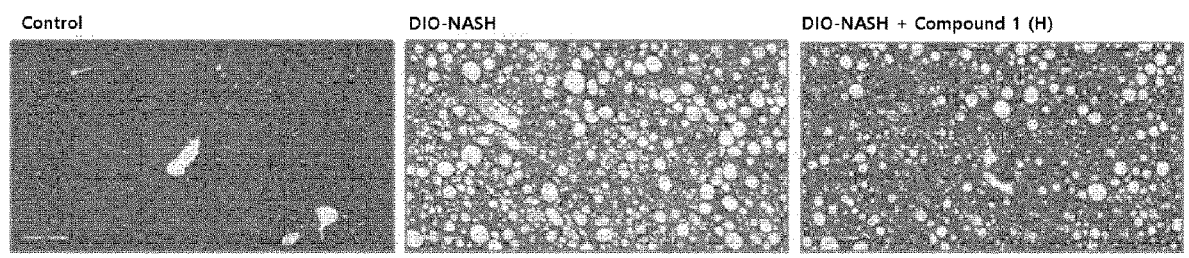
FIG. 10 is a picture of a tissue sample showing an effect of reducing triglycerides and inhibiting infiltration of inflammatory cells in liver tissues by the compound of the present invention in a mouse model with induced non-alcoholic steatohepatitis.

For a histological examination, the prepared C57BL/6J mouse model was subjected to autopsy to fix an isolated liver tissue in 10% formalin and prepare a paraffin block, thereby obtaining a 2 µm-thick tissue section. Then, Hematoxylin and Eosin (HE) stain was performed using an automatic staining machine (Autostainner XL, Leica), and the results thereof are shown in FIG. 10. In addition, the liver tissue isolated from the C57BL/6J mouse model was used to measure a content of triglycerides in the liver tissue by using a Triglyceride reagent (Roche Diagnostics, #22-045-795), and the results are shown in FIG. 11.

Figure 11:
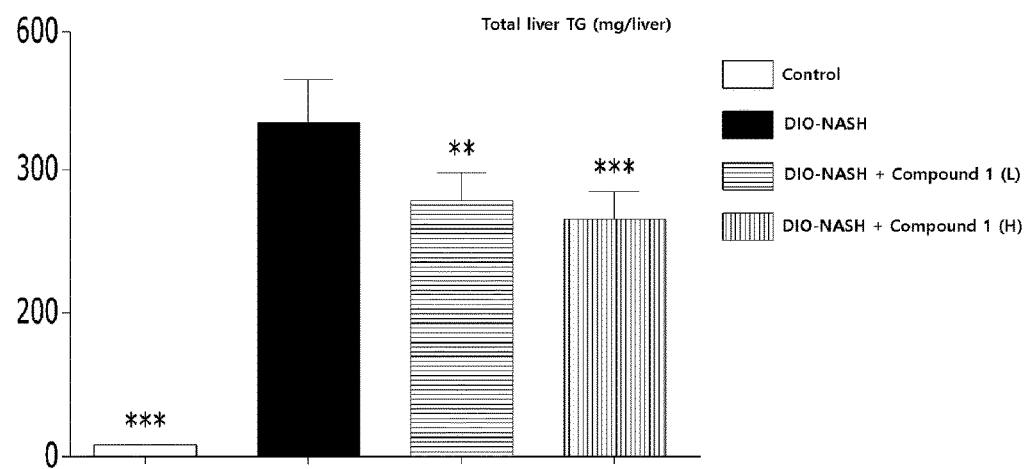
FIG. 11 is a view showing results of measuring a content of triglycerides in liver tissues in a mouse model with induced non-alcoholic steatohepatitis ( & *, $p<0.01$ & $p<0.001$ vs. DIO-NASH).

As understood from FIGS. 10 and 11, the mice fed with a special diet only (DIO-NASH) showed a remarkable increase in fat deposits and infiltration of inflammatory cells in liver tissues compared to the mice fed with a normal diet (Normal), while the DIO-NASH_Compd1 (H) group fed with the compound 1 of the present invention together with the special diet showed a significant decrease in fat deposits and infiltration of inflammatory cells.

Figure 12:
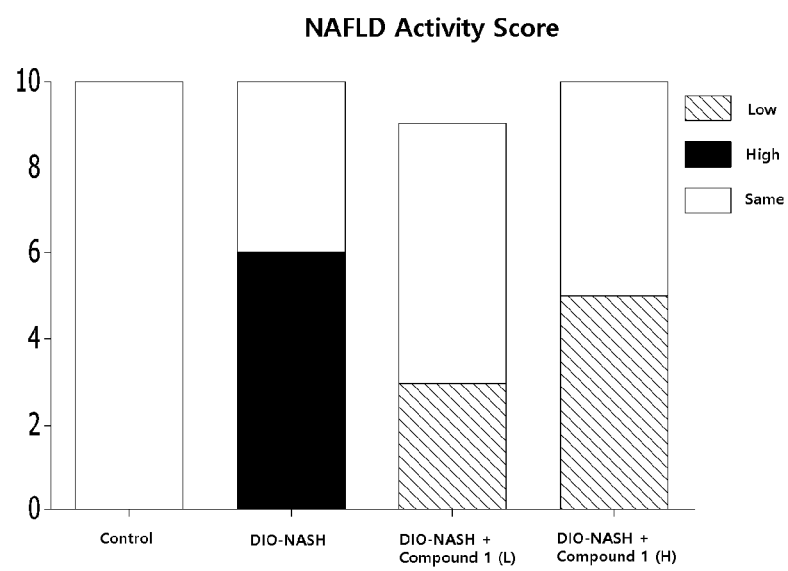
FIG. 12 is a view showing a change in NAFLD activity score (NAS) before and after administration into the same individual in a mouse model with induced non-alcoholic steatohepatitis.

In addition, as a result of calculating an NAFLD activity score (NAS) reflecting a ratio of fat cells, infiltration of inflammatory cells and damage to hepatocytes based on the above histological examination, before and after administration, the disease worsened in 50% of the DIO-NASH group, while no individual was deteriorated in case of administering the compound, and the disease was ameliorated in about 50% of the DIO-NASH_Compd1 group (FIG. 12).

Figure 13:
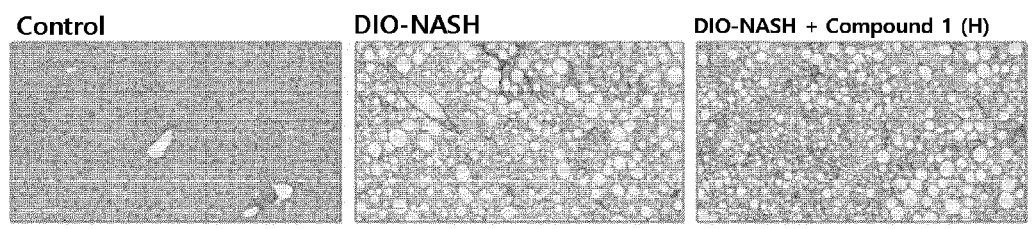
FIG. 13 is a picture of a tissue sample showing an effect of inhibiting fibrosis by the compound of the present invention in a mouse model with induced non-alcoholic steatohepatitis.
Figure 14:
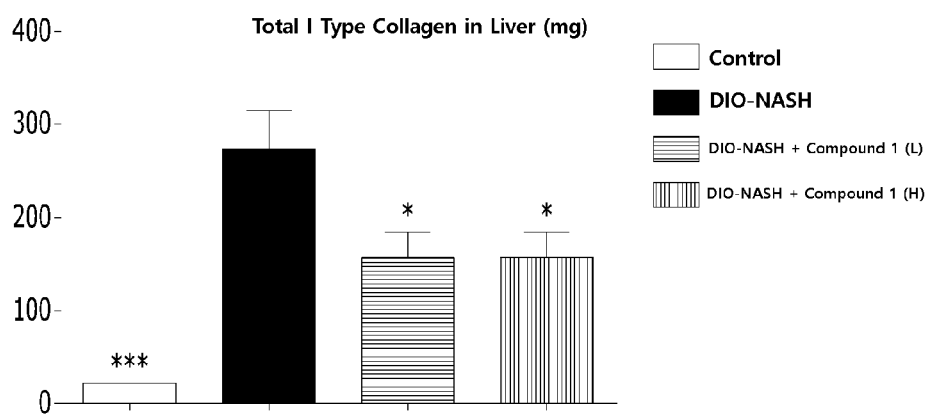
FIG. 14 is a view showing results of measuring a content of type I collagen in liver tissues in a mouse model with induced non-alcoholic steatohepatitis (* & ***, $p<0.05$ & $p<0.001$ vs. DIO-NASH).

Then, for the evaluation of fibrosis, the fibers of the liver tissues were specifically stained with Sirius Res stain in the mice of each group, and a content of type I collagen in the liver tissues was measured by an imaging analysis method after immunostaining, so that the results thereof are shown in FIGS. 13 and 14.

As shown in FIGS. 13 and 14, the mice fed with the special diet only (DIO-NASH) showed a remarkable progress of fibrosis in liver tissues compared to the mice fed with the normal diet (Normal), while the group fed with the compound 1 of the present invention together with the special diet (DIO-NASH_Compd1) showed a remarkable decrease in a cross-linking formation in fibers of the liver tissues and also showed a significant decrease in type I collagen.

AST and ALT Measurement in Blood

Each of the mouse groups was subjected to autopsy, after which plasma was separated therefrom, so as to quantity aspartate aminotransferase (AST) and alanine aminotransferase (ALT) by using an automatic blood analyzer (Konelab 20i). Thus, the results thereof are shown in FIG. 15.

Figure 15:
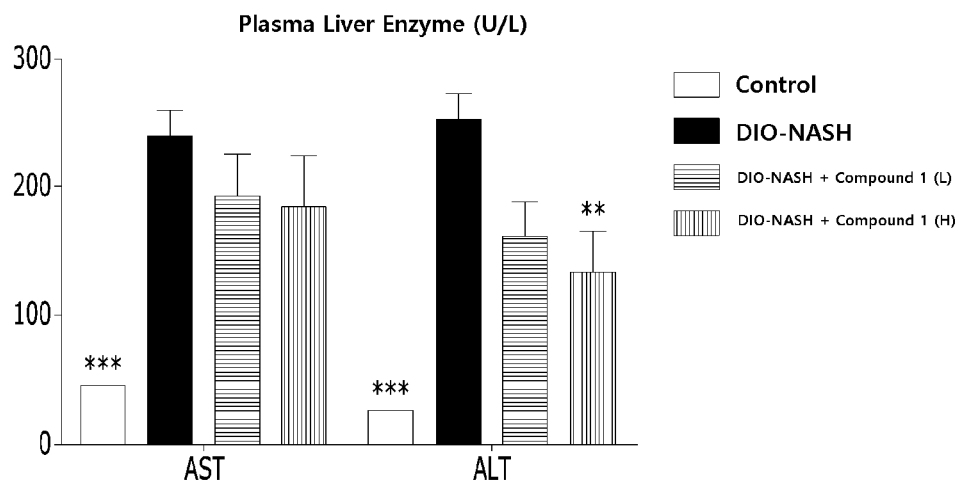
FIG. 15 is a view showing results of measuring a concentration of AST and ALT in blood in a mouse model with induced non-alcoholic steatohepatitis ( & *, $p<0.01$ & $p<0.001$ vs. DIO-NASH).

As shown in FIG. 15, the group of mice fed with the special diet only (DIO-NASH) showed a significant increase in a concentration of ALT and AST in blood compared to the mice fed with the normal diet, while the group of mice fed with the compound 1 of the present invention together with the special diet (DIO-NASH_Compd1) showed a significantly inhibited increase in ALT and AST.

Confirmation of Change in Gene Expression

Figure 16:
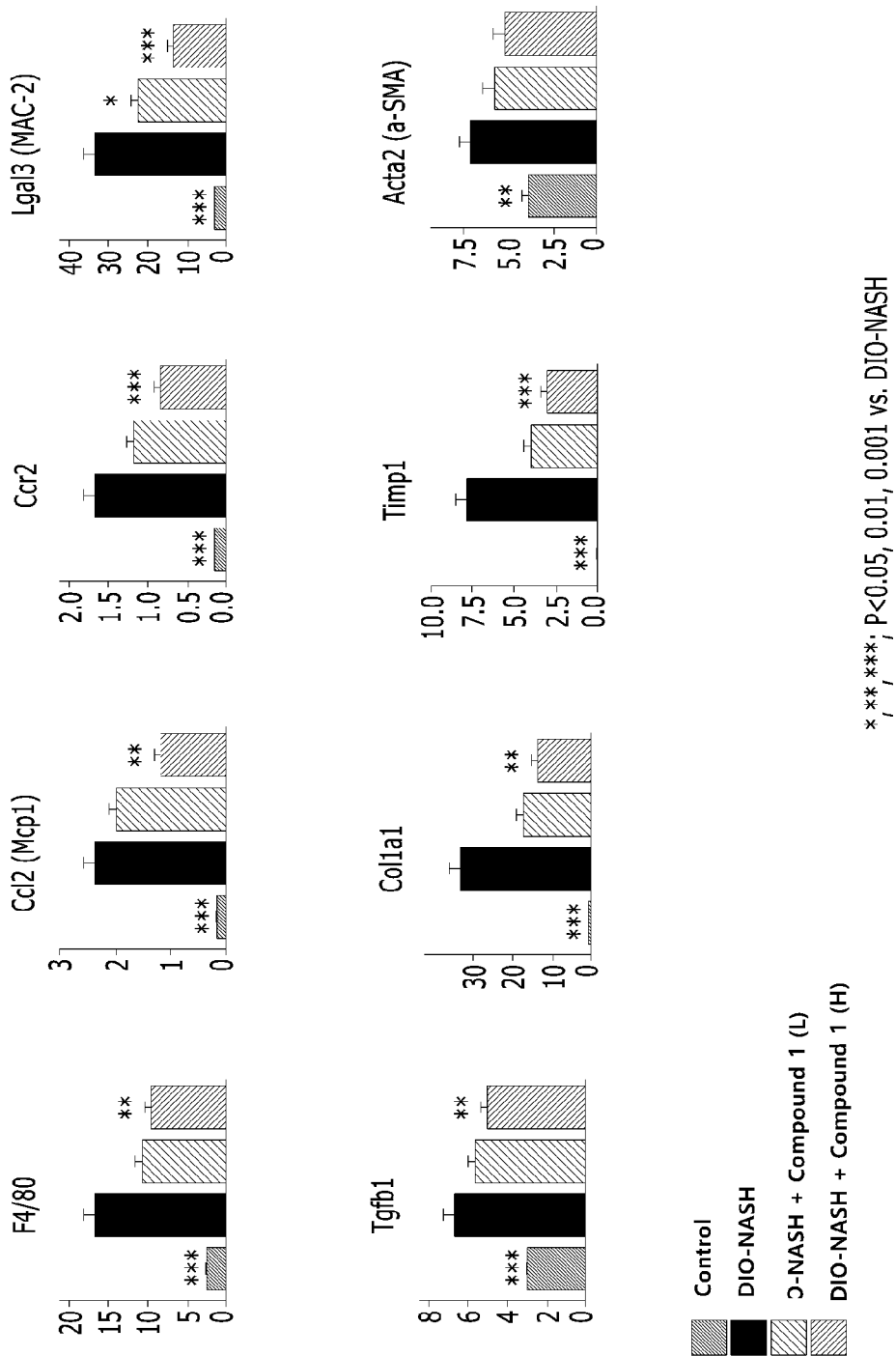
FIG. 16 is a view showing results of measuring a gene expression level of monocyte attractant, macrophage markers and fibrosis markers in liver tissues of a mouse model with induced non-alcoholic steatohepatitis (*,  & *, $p<0.05$, $p<0.01$ & $p<0.001$ vs. DIO-NASH).

To analyze a change in total gene expression in liver tissues isolated from the above mouse model in eight weeks after drug administration, the isolated RNA fraction was used to generate a library by using NeoPrep (Illumina), and subjected to RNAseq profiling through NexSeq 500 (Illumina), after which bioinformatics analysis was performed and changes in major gene groups were classified for each function, so that the results thereof are shown in FIG. 16.

As shown in FIG. 16, the mice fed with the special diet only (DIO-NASH) showed an increase in the expression of monocyte attractants, macrophage markers and fibrosis markers in liver tissues compared to the mice fed with the normal diet (Normal), while the DIO-NASH_Compd1 group of mice fed with the compound 1 of the present invention together with the special diet showed a remarkable decrease in the above markers.

The above results suggest that the compound of the present invention has an effect on non-alcoholic fatty liver disease by inhibiting the damage, inflammation and fibrosis of liver tissues, and has a more excellent therapeutic effect by co-administering a DPPIV inhibitor.

The invention claimed is:

1. A method for alleviating, or treating non-alcoholic steatohepatitis, the method comprising administering to a subject in need thereof a therapeutically effective amount of a composition, comprising a compound represented by a following chemical formula 1, pharmaceutically acceptable salts thereof, optical isomers thereof, hydrates or solvates thereof, or mixtures thereof as an effective ingredient:

[Chemical Formula 1]

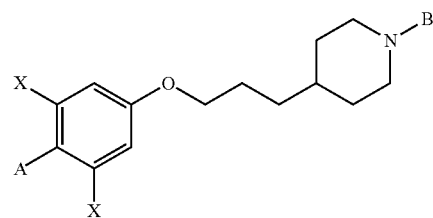

wherein A is

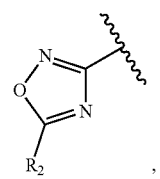

$R_2$ is C1-C6 straight or branched-chain alkyl;

B is

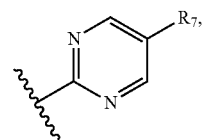

$R_7$ is C1-C6 straight or branched-chain alkyl; and each X is F.

2. The method of claim 1, wherein the composition inhibits deposition of triglycerides in liver tissues.

3. The method of claim 1, wherein the composition inhibits infiltration of inflammatory cells in liver tissues.

4. The method of claim 1, wherein the composition inhibits fibrosis of liver tissues.

5. The method of claim 1, wherein the compound represented by the chemical formula 1 is 3-(4-(3-(1-(5-ethylpyrimidine-2-yl)piperidine-4-yl) propoxy)-2,6-difluorophenyl)-5-isopropyl-1,2,4-oxadiazole.

* * * * *